United States Patent [19]

Wilson et al.

[11] Patent Number: 4,859,463

[45] Date of Patent: * Aug. 22, 1989

[54] USE OF METHYL-ISOEUGENOL, N-DODECANOL AND MIXTURES OF SAME AS INSECT ATTRACTANTS

[75] Inventors: Richard A. Wilson, Westfield, N.J.; Jerry F. Butler, Gainesville, Fla.; Donald Withycombe, Lincroft, N.J.; Braja D. Mookherjee, Holmdel, N.J.; Ira Katz, West Long Branch, N.J.; Kenneth R. Schrankel, Tinton Falls, N.J.

[73] Assignees: International Flavors & Fragrances Inc., New York, N.Y.; The University of Florida, Gainesville, Fla.

[*] Notice: The portion of the term of this patent subsequent to Jan. 31, 2006 has been disclaimed.

[21] Appl. No.: 213,682

[22] Filed: Jun. 30, 1988

Related U.S. Application Data

[63] Continuation of Ser. No. 930,418, Nov. 14, 1986, Pat. No. 4,801,446.

[51] Int. Cl.$^4$ ............... A01N 25/00; A01N 31/00; A61K 31/74; A61K 31/78
[52] U.S. Cl. .......................... 424/84; 424/78; 424/81; 514/724; 514/733
[58] Field of Search ............... 424/84, 78, 81; 514/724, 733

[56] References Cited

U.S. PATENT DOCUMENTS 4,059,689 11/1987 Struble et al. ............... 424/84

OTHER PUBLICATIONS

Qureshi et al. Pakistan J Sci. ind res, vol. 19 No. 1 Feb. 1976.

Primary Examiner—Douglas W. Robinson
Assistant Examiner—Joseph A. Lipovsky
Attorney, Agent, or Firm—Arthur L. Liberman

[57] ABSTRACT

Described are the uses of methyl-isoeugenol having the structure:

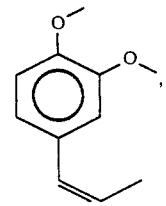

n-dodecanol having the structure:

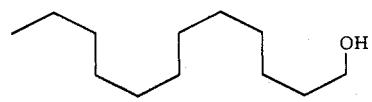

and 1-(2-butenoyl)-2,6,6-trimethyl-1,3-cyclohexadiene having the structure:

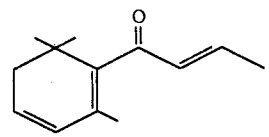

taken alone or taken in combination as attractants house flies (Musca domestica L. (Diptera:Muscidae)) and Stored Products Moths. The methyl-isoeugenol, n-dodecanol and 1-(2-butenoyl)-1,3-cyclohexadiene taken alone or in combination find utility primarily as bait enhancers for acute toxins and/or trapping devices.

8 Claims, 6 Drawing Sheets

USE OF METHYL-ISOEUGENOL, N-DODECANOL AND MIXTURES OF SAME AS INSECT ATTRACTANTS

This is a continuation of application Ser. No. 930,418, filed 11/14/86 now U.S. Pat. No. 4,801,446.

BACKGROUND OF THE INVENTION

This invention relates to insect attractants for house flies (*Musca domestica* L. (Diptera:Muscidae) and Stored Products Moths. More particularly this inventio relates to compositions of matter containing methyl-isoeugenol, n-Dodecanol and 1-(2-Butenoyl)-2,6,6-Trimethyl-1,3-Cyclohexadiene or combinations of methyl-isoeugenol, n-Dodecanol and 1-(2-Butenoyl)-2,6,6-Trimethyl-1,3-Cyclohexadiene as attractants for *Musca domestica* L. (Diptera:Muscidae) and Stored Products Moths.

Fast intercontinental travel and trade are stepping up changes of importing nonindigenous insect pests into the United States. Attractants, or lures, can be of considerable aid in facilitating the early detection of such insect pests, and they are of vital importance in measuring the progress of a program aimed at eradicating a species that has become established.

In Agriculture Handbook No. 239 published by the Agricultural Research Service of the United States of America Department of Agriculture issued in June 1963 entitled, "Materials Tested As Insect Attractants", compiled by M. Beroza and N. Green, Eugenol having the structure:

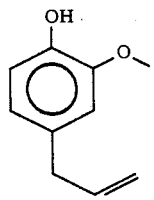

is indicated to have a very high attractancy index ("3" on a scale of 1 to 3 for the Oriental Fruit Fly and "1" on a scale of 1 to 3 for Mediterranean Fruit Fly. n-Dodecanol is indicated in the Agriculture Handbook No. 239 to attract the Oriental Fruit Fly, the Melon Fly, the Mediterranean Fruit Fly and the Mexican Fruit Fly only slightly ("1" on a scale of 1 to 3). Decanol-1 having the structure:

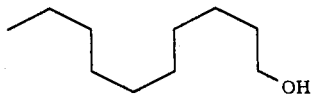

is indicated to attract the Oriental Fruit Fly at a level of "1" on a scale of 1 to 3; the Melon Fly at a level of "2" on a scale of 1 to 3; the Mediterranean Fruit Fly at a level of "1" on a scale of 1 to 3; and the Mexican Fruit Fly at a level of "1" on a scale of 1 to 3.

However, nothing in the prior art discloses the use of methyl-isoeugenol, n-Dodecanol or 1-(2-Butenoyl)-2,6,6-Trimethyl-1,3-Cyclohexadiene taken alone or in combination in attracting certain species of insects including *Musca domestica* L. (Diptera:Muscidae) or Stored Products Moths.

SUMMARY OF THE INVENTION

Figure 1:
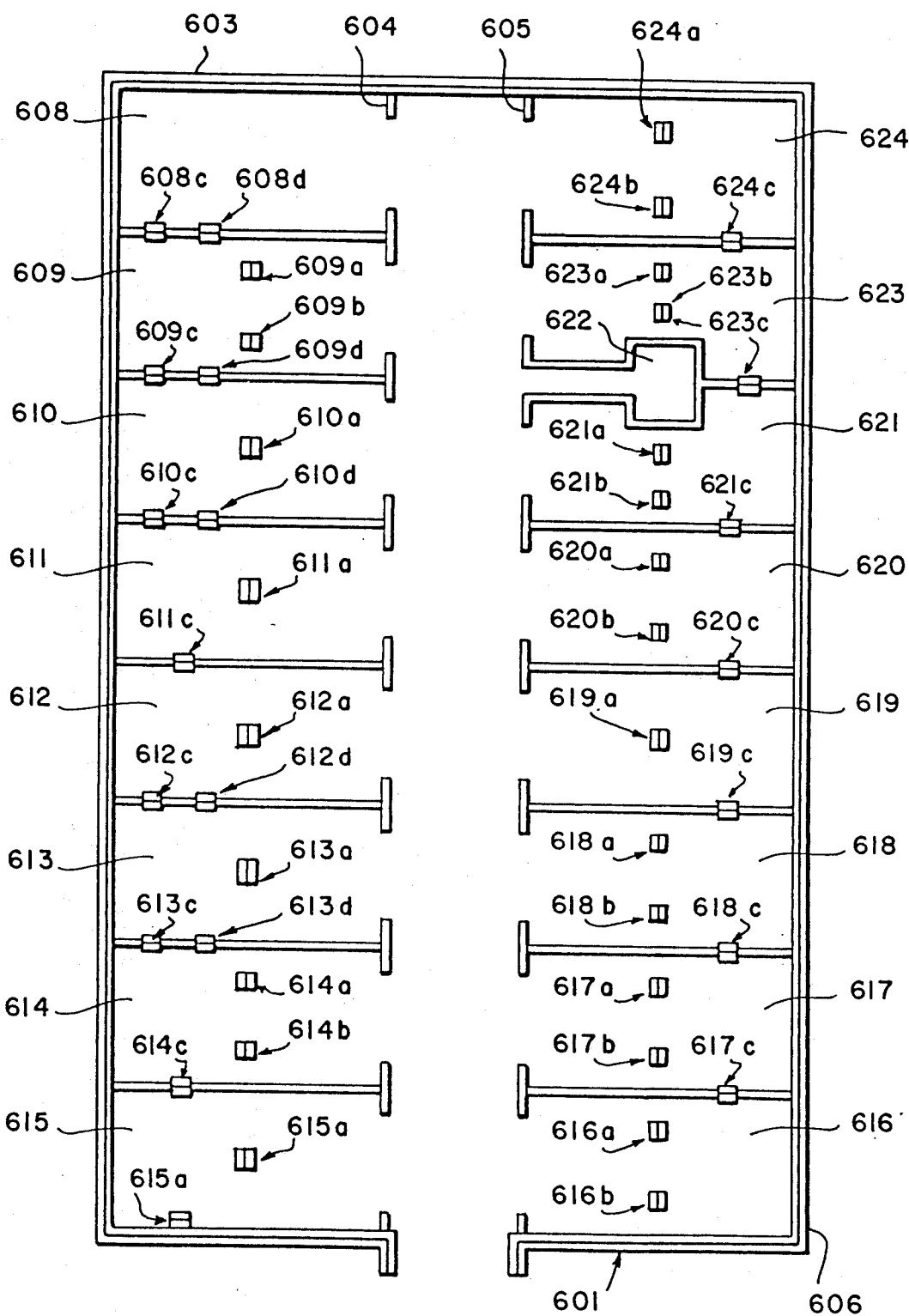
FIG. 1 is a schematic top view of the location of insect traps containing formulated slow release insect attractants and control materials (known attractant, GOLDEN MALRIN ® fly baid).

Our invention relates to the use of methyl-idoeugenol, n-Dodecanol or 1-(2-Butenoyl)-2,6,6-Trimethyl-1,3-Cyclohexadiene or combinations thereof, e.g., mixtures of methyl-isoeugenol and n-Dodecanol, mixtures of methyl-isoeugenol and 1-(2-Butenoyl)-2,6,6-Trimethyl-1,3-Cyclohexadiene and mixtures of n-Dodecanol and 1-(2-Butenoyl)-2,6,6-Trimethyl-1,3-Cyclohexadiene or mixtures of methyl-isoeugenol, n-Dodecanol and 1-(2-Butenoyl)-2,6,6-Trimethyl-1,3-Cyclohexadiene as attractants for house flies (*Musca domestica* L. (Diptera:Muscidae)) and Stored Products Moths. A trapping system which is the basis of a first testing technique used in testing the efficacy of the methyl-isoeugenol, n-Dodecanol, 1-(2-Butenoyl)-2,6,6-Trimethyl-1,3-Cyclohexadiene and combinations thereof is a standard ZOECON ® sticky trap consisting of a ZOECON PHEROCON ® 1C trap with a 2 cm×2 cm strip of formulated slow release attractant suspended on a paper clip inside the trap. The traps were placed in a goat barn and are suspended from the rafters. Trap placement was replicated in the four quadrants of the barn. Traps were placed in the barn for seven days and the insects collected were identified and counted. Evidence of insects visiting the traps were also counted as insect specks inside the traps. All test materials were compared with a standardized check treatment consisting of 0.5 grams of GOLDEN MALRIN ® fly bait inside of the slow release packet hung like other compounds.

A second testing technique concerns the electrophysiological study of the neural corrolates of attraction and repulsion in *Musca domestica L.* (Diptera:Muscidae)(house flies). Different points in the house fly olfactory neuroarchitecture were studied using electrophysiology in an effort to identify the neural corrolates of attractant and repellent signals resulting from potentially attractant and repellent substances.

Recordings from the antennal lobe of the deuterocerebrum of the *Musca domestica L.* (Diptera:Muscidae) showed that the repellent signals were highly distinguishable from the attractant signals. Signals from repellents showed a shift in base line potential of approximately 25 m Volts whereas attractant signals (e.g., in the case of methyl-isoeugenol) showed no shift.

Thus, neural signals of the antennal lobe are used herein as an assay for olfactory canvassing to predict behavioral activity of the *Musca domestica L.* (Diptera:Muscidae) (house fly).

Our invention also relates to the formation of insect attractant-containing polymeric pellets by means of introduction into a single screw or twin screw extruder of, in series, thermoplastic polymer followed by insect attractant which is compatible with the thermoplastic polymer, in turn, followed by introduction of a gaseous blowing agent or blowing agent which will produce a gas which is inert to the polymer and to the insect attractant, e.g., methyl-isoeugenol, n-Dodecaol or 1-(2-Butenoyl)-2,6,6-Trimethyl-1,3-Cyclohexadiene or combinations thereof.

In the alternative, the use of the foaming agent can be omitted.

The nature of the extruder utilized in this aspect of our invention to form the polymeric insect attractant particles of our invention may be either single screw or double screw. Thus, the types of extruder that can be used are disclosed at pages 246–267 and 332–349 of the Modern Plastics Encyclopedia, 1982–1983 published by the McGraw-Hill Publishing Company, the disclosure of which is incorporated by reference herein. More specifically, examples of extruders which are useable in carrying out this aspect of our invention (with modification for introduction of insect attractant downstream from introduction of the polymer and optionally with a further modification that the gaseous blowing agent is introduced still further downstream from the point of introduction of insect attractant) are as follows:

1. The Welex "Super Twinch" 3.5" extruder manufactured by Welex Incorporated, 850 Jolly Road, Blue Bell, Pa. 19422;
2. Krauss-Maffei twin screw extruder manufactured by the Krauss-Maffei Corporation/Extruder Division, 3629 West 30th Street South, Witchita, Kans. 67277;
3. Modified Sterling Model 4000 and 5000 series extruder manufactured by Sterling Extruder Corporation of 901 Durham Avenue, South Plainfied, N.J.;
4. CRT ("Counter-Rotating Tangential") Twin Screw Extruder manufactured by Welding Engineers, Inc. of King of Prussia, Pa. 19406;
5. The Leistritz Twin Screw Dispersion Compounder manufactured by the American Leistritz Extruder Corporation of 198 U.S. Route 206 South, Somerville, N.J. 08876;
6. The ZSK Twin Screw Co-Rotating Extruder manufactured by the Werner & Pfleiderer Corporation of 663 East Crescent Avenue, Ramsey, N.J. 07446;
7. The Farrel Extruder manufactured by Farrel Connecticut Division, Emhart Machinery Group, Ansonia, Conn. 06401;
8. The MPC/V Baker Perkins Twin Screw Extruder manufactured by the Baker Perkins Inc. Chemical Machinery Division of Saginaw, Mich. 48601; and
9. The Berstorff Single Screw, Twin Screw, or Foam Extrusion Equipment manufactured by Berstorff Corporation, P. O. Box 240357, 8200-A Arrowridge Boulevard, Charlotte, N.C. 28224.

In producing the insect attractant-containing polymer particles of our invention, various polymers may be utilized, for example, low density polyethylene, high density polyethylene, polypropylene, the co-polymer of ethylene and vinyl acetate, and polyvinyl chloride. More specifically, the polymers used in the practice of our invention may be co-polymers of ethylene and a polar vinyl monomer selected from (a) vinyl acetate; (b) ethyl acrylate; (c) methyl acrylate; (d) butyl acrylate and (e) acrylic acid including the hydrolyzed co-polymer of ethylene and vinyl acetate. Preferred co-polymers are ethylene vinyl acetate with about 9 to 60% vinyl acetate and ethylene/ethyl acrylte with about 6 to 18% ethyl acrylate.

Resins of the type disclosed for use as co-polymers are commercially available in the molding powder form. For example, ethylene vinyl acetate co-polymers are marketed by the E. I. duPont de Nemours Company under the tradename "ELVAX ®" and by the Arco Polymer Division under the trademark "DYLAND" and by the Exxon Corporation of Linden, N.J. under the trademark "DEXXON". Ethylene/ethyl acrylate co-polymers are marketed by Union Carbide Corporation under the tradename "EEA RESINS".

The polymer is added to the single screw or twin screw extruder at a feed rate in the range of from about 80 up to about 300 pounds per hour while maintaining the temperature in the screw extruder between about 160° and about 240° C. If the polymer or co-polymer powder is added to the extruder at a reference "barrel segment", then the insect attractant is added to the extruder under pressure downstream from the addition point of the polymer at 1 or more "barrel segments" S-2, S-3, S-4, S-5, S-6, S-7, S-8 or S-9.

Thus, the invention provides a process for forming insect attractant-containing polymeric particles such as polymeric pellets which include a relatively high concentration of insect attractants. The insect attractant added at "barrel segments" "S-2, S-3, S-4, S-5, S-6, S-7, S-8 or S-9 of the single screw or twin screw extruder is to be compatible with the polymer added at "barrel segment" S-1 of the single screw or twin screw extruder.

The proportion of insect attractant is limited only by either (a) it solubility in the resin or mixture of resins used and/or (b) the volume ratio of microvoids in the polymer to said polymer and/or (c) the solubility of the insect attractant in the polymer on solidification. The proportion of insect attractant can in many instances go up to 45% by weight or even higher.

Thus, the proportion of insect attractant to resin can vary from small but effective amounts on the order of about 1% of the weight of the resin body up to about 45% by weight of the resin body. In general, it is preferred to use between about 5% up to about 30% based on the weight of resin body of the insect attractant. This is an optimum amount balancing the proportion of insect attractant against the time period over which the article emits the insect attractant and against the tendency of the insect attractant to "oil out". This "oiling out" is specifically avoided as a result of the use of foaming agent.

As stated, supra, various polymers are useful in the practice of our invention. Specific examples of polymers useful in the practice of our invention are as follows:

(a) DYLAN® brand of low density polyethylene DYLAN® is a trademark owned by the Atlantic Richfield Company of Los Angeles, Calif.;

(b) DYLITE® of expandable polystyrene compositions. DYLITE® is a trademark of the Atlantic Richfield Company of Los Angeles, Calif.;

(c) SUPER DYLAN® a high density polyethylene. SUPR DYLAN® is a tradmark of the Atlantic Richfield Company of Los Angeles, Calif.;

(d) Blended polyethylene and carbon black as specifically taught in U.S. Pat. No. 4,369,267 issued on Jan. 18, 1983, the specification for which is incorporated by reference herein;

(e) Polystyrene as disclosed in U.S. Pat. No. 4,369,227 issued on Jan. 18, 1983, the specification for which is incorporated herein;

(f) Polyene/alpha-olefin as exemplified and disclosed in U.S. Pat. No. 4,369,291, the specification for which is incorporated by reference herein;

(g) Poly-alpha-olefins as exemplified in Canadian Letters Pat. No. 1,137,069 issued on Dec. 7, 1982, the specification for which is incorporated herein;

(h) Polymeric compositions as disclosed in Canadian Letters Pat. No. 1,137,068 issued on Dec. 7, 1982, the specification for which is incorporated by reference herein;

(i) Poly-alpha-olefins disclosed in Canadian Letters Pat. No. 1,137,067, the specification for which is incorporated by reference herein;

(j) Polyolefins described in Canadian Letters Pat. No. 1,137,066, the specification for which is incorporated by reference herein;

(k) Polyethylene oxides as disclosed in Canadian Letters Pat. No. 1,137,065 issued on Dec. 7, 1982, the specification for which is incorporated by reference herein;

(l) Olefin polymers and co-polymers as disclosed in Canadian Letters Pat. No. 1,139,737, the disclosure of which is incorporated by reference herein. Canadian Pat. No. 1,139,737 was issued on Jan. 18, 1983;

(m) Polyolefins disclosed in Canadian Letters Pat. No. 1,139,738, the disclosure of which is incorporated by reference herein. Canadian Pat. No. 1,139,738 was issued on Jan. 18, 1983;

(n) Chlorinated PVC as disclosed in *Polymer* 1982, 23 (7, Suppl.), 1051–6 abstracted at Chem. Abstracts 97:145570y, 1982;

(o) Polyepsilon caprolactone co-polymers made by means of alcohol initiated polymerization as disclosed by *J. Polym. Sci. Polym. Chem. Ed.* 1982, 20(2), pages 319–26, abstracted at Chem. Abstracts, Volume 96:123625x, 1982;

(p) Styrene acrylonitrile co-polymers as disclosed in Diss. Abstracts, Int. B, 1982, 42(8), 3346 and abstracted at Chem. Abstracts 96:143750n (1982);

(q) Co-polymers of epsilon caprolactone with 1,4-butane diol as disclosed at Kauch. Rezine, 1982, (2), 8–9, abstracted at Chem. Abstracts, Volume 96:182506g (1982);

(r) Polyesters as disclosed in U.S. Pat. No. 4,326,010, the specification for which is incorporated by reference herein;

(s) Chlorinated polyethylene as disclosed by Belorgey, et al, *J. Polym. Sci. Polym. Phys. Ed.* 1982, 20(2), 191–203;

(t) Plasticized polyepsilon caprolactone co-polymers containing dimethyl phthalate plasticizers as set forth in Japanese Pat. No. J81/147844, abstracted at Chem. Abstracts, Volume 96:69984y (1982), the specification for which is incorporated by reference herein;

(u) Maleic anhydride modified adducts of polyepsilon caprolactone polyols and ethyleically unsaturated monomer as disclosed in U.S. Pat. No. 4,137,279 issued on Jan. 30, 1979, the specification for which is incorporated by reference herein;

(v) Polyurethane polymers having lactone backbones as disclosed in U.S. Pat. No. 4,156,067 issued on May 22, 1979, the disclosure of which is incorporated by reference herein;

(w) Polyurethane polyether resins wherein the resin is obtaied by reacting a polyfunctional lactone with a long chain polyalkylene diol and a urethane precursor as disclosed in U.S. Pat. No. 4,355,550 issued on Mar. 10, 1981, the disclosure of which is incorporated by reference herein; and (x) Resins having polyurethane backbones as disclosed in U.S. Pat. No. 3,975,350 issued on Aug. 17, 1976, the disclosure of which is incorporated by reference herein.

Optionally, downstream from the addition point of the insect attractant a gaseous or liquid containing blowing agent may be added (e.g., at barrel segments S-5, S-6, S-7, S-8 or S-9 and S-10) using the polymer addition barrel segment as a reference barrel segment "S-1". Examples of gaseous blowing agents are carbon dioxide, nitrogen, mixtures of nitrogen and carbon dioxide in proportions of from 1 up to 99% by volume nitrogen and 99 down to 1% by volume carbon dioxide, helium, mixtures of helium and nitrogen, mixtures of helium and carbon dioxide and other gases which are inert at the temperature and pressure of the polymer at the time of the extrusion operation. Thus, gas containing oxygen or other reactive gases, e.g., hydrogen, should be avoided. The pressure of the gas blowing agent being added to the extruder at the point of addition may vary from about 80 up to about 150 psig. Higher pressures may be used without adversely affecting the usefulness of the foamed insect attractant-containing polymer particle.

The feed rate range of insect attractant may be between about 0.5% up to about 45% by weight of the polymer.

The die of the extruder may create rod, sheet, film or ribbon. The resulting product may then, if desired, be pelletized to form foamed insect attractant-containing polymer particles or the ribbon maybe used "as-is" as an insect attractant-containing polymeric article of manufacture itself.

In addition to the optional gaseous blowing agents (which are necessarily "inert" gases), blowing agents may be added at some point on the extruder which will create gaseous voids in the insect attractant-containing polymeric articles of our invention and these "blowing agents" are well known to one having ordinary skill in the art. Examples of such non-gaseous containing materials which yield gases on admixture with the polymer in the extruder but which are still inert to the insect attractant are as follows:

(i) Under high pressure, ethylene, methane, propane, butane, propylene, methyl chloride, methyl bromide, vinyl chloride and methylene dichloride as more specifically described in U.S. Pat. No. 2,387,730, the specification for which is incorporated by reference herein;

(ii) Ordinarily liquid material such as n-pentane, isopentane, cyclopentane, hexane and petroleum ether fractions or halogen hydrocarbons such as $CFCl_3$, $CF_2Cl_2$, $CH_3Cl$, $CH_2Cl_2$ separately or in admixture with one another as set forth in U.S. Pat. No. 3,758,425, column 4, lines 1–5, the specification for which is incorporated by reference herein;

(iii) Dichlorotetrafluoroethane, tetramethylmethane, monochlorodifluoromethane, dichlorodifluoromethane, and dichlorotetrafluoroethane as specifically described in U.S. Pat. Nos. 2,948,664 and 2,948,665 issued on Aug. 9, 1960, the specifications for which are incorporated herein by reference; and (iv) Azo bis(formamide); diazoaminobenzene; N,N'-dinitrosopentamethylene tetramine; N,N'-dimethyl-N,N'-dinitrosoterephthalamide; p,p'-oxy-bis(benzene sulfonyl semicarbazide); azo bis(isobutyronitrile); p,p'-oxy-bis(benzene sulfonyl hydrazide); p,p'-diphenyl-bis(sulfonyl hydrazide); benzene-sulfonyl hydrazide); m-benzene-bis(sulfonyl hydrazide) as more specifically described in U.S. Pat. No. 3,298,975 issued on Jan. 17, 1967, the specification for which is incorporated by reference herein.

The resulting extruded (and if desired pelletized) material may then be, for example, injection molded to form a useful article. Such injection molding can be carried out in accordance with the procedure as set forth in U.S. Pat. No. 3,268,636 issued on Aug. 23, 1966, the specification for which is incorporated by reference herein.

DETAILED DESCRIPTION OF THE DRAWINGS

Referring to FIGS. 1, 2, 3 and 4, FIGS. 3 and 4 shown in detail the ZOECON ® sticky trap, more specifically a Zoecon Pherocon 1C Trap (e.g., in FIG. 4 indicated by reference numeral 616a) and in FIG. 1 indicated by reference numerals 608c, 608c, 609a, 609b, 609c, 609d, 610a, 610c, 610d, 611a, 611c, 612c, 612d, 613a, 613c, 613d, 614a, 614b, 614c, 615a, 615c, 616a, 616b, 617a, 617b, 617c, 618a, 618b, 618c, 619c, 620a, 620b, 620c, 621a, 621b, 621c, 623a, 623b, 623c, 624a, 624b, and 624c. The Zoecon Pherocon 1C Trap has suspended in it as will be seen from FIGS. 3 and 4, a 2 cm×2 cm strip of slow release polymer (polyethylene) 6117 in FIGS. 3 and 4 containing insect attractant (methyl-isoeugenol, n-Dodecanol or 1-(2-Butenoyl)-2,6,6-Trimethyl-1,3-Cyclohexadiene or mixtures thereof containing from about 0.5% up to about 99% by weight of methyl-isoeugenol; from about 99% down to about 0.5% by weight of n-Dodecanol; and from about 0.5% up to about 99% by weight of 1-(2-Butenoyl)-2,6,6-Trimethyl-1,3-Cyclohexadiene) or the 2 cm×2 cm strip contains the GOLDEN MALRIN ® control. The 2 cm×2 cm strip 6117 is suspended in the trap 616a from bar 6116 using holder 6118. Trap 616a has lower tray 6110 which will catch insect droppings or dead insects which do not adhere to the 2 cm×2 cm strip 6117. The lower tray 6110 is attached via strips 6112a and 6112b to upper holder 6111 which is attached to suspension bar 6113 suspended by rod 6114 to the barn beam 6115 (in FIG. 2). The barn beam 6115 is held in a horizontal position by upright suppots 602 and 606 (as will be seen in FIG. 2) which is firmly in place on the barn floor 6119. The 2 cm×2 cm strip 6117 is formulated in such apparatus as is set forth in FIG. 11 described in detail, infra. The traps containing the insect attractant, e.g., methyl-isoeugenol, n-Dodecanol or 1-(2-Butenoyl)-2,6,6-Trimethyl-1,3-Cyclohexadiene or combinations thereof or the GOLDEN MARLIN ® control are placed in the goat barn having fencing panels 601 and 603 and inner support 604 and 605, an observation post 622 and experimental locations 608, 609, 610, 611, 612, 613, 614, 615, 616, 617, 618, 619, 620, 621, 623 and 624 has suspended in it the several Zoecon Pherocon 1C Traps each containing 2 cm×2 cm strips of formulated slow release insect attractants. Trap placement was replicated in four quadrants of the barn. Traps 616a, 616b, 615a, 615c and other traps were placed in the barn for seven days and the insects collected were identified and counted. Evidence of various insects visiting the traps were also counted, as fly specks inside or outside to the traps. All the test materials were compared with a standardized check treatment consisting of 0.5 grams of GOLDEN MALRIN ® fly bait inside slow release packets hung like the other compounds as in strip 6117 in FIGS. 3 and 4.

Figure 5:
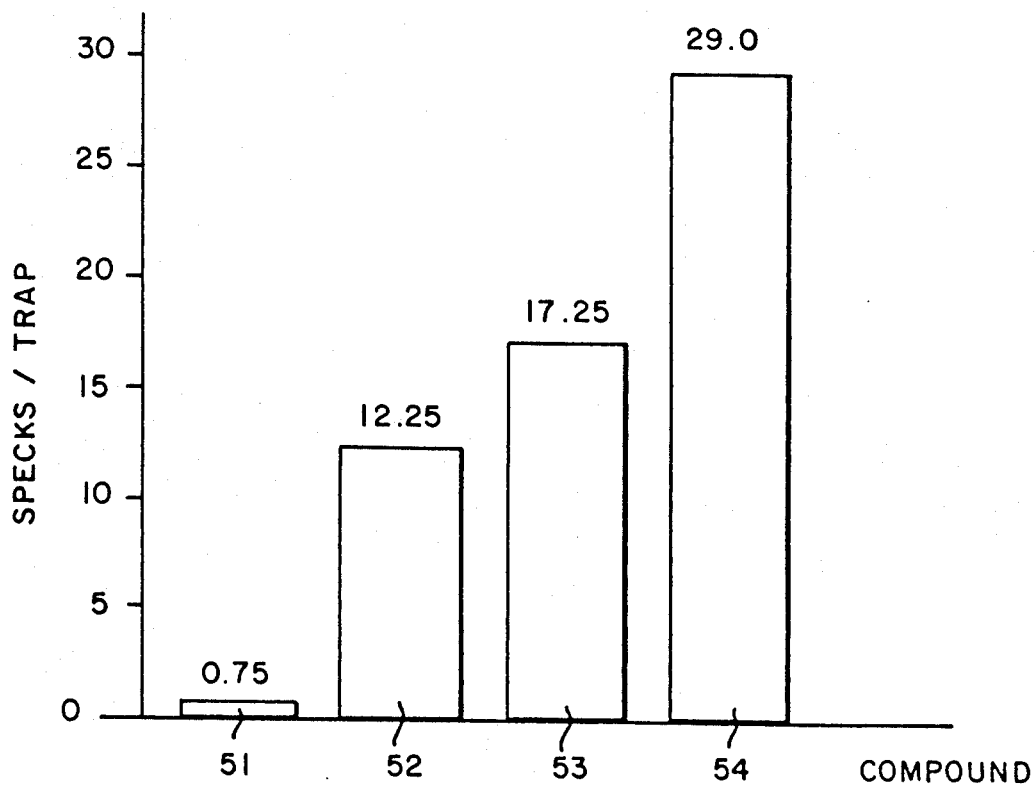
FIG. 5 is a bar graph showing a comparison of the field trial tests of attractants for house flies (*Musca domestica* L. (Diptera:Muscidae)) comparing methyl-isoeugenol, n-Dodecanol and 1-(2-Butenoyl)-2,6,6-Trimethyl-1,3-Cyclohexadiene and GOLDEN MARLIN ® a mixture of (Z)-9-tricosene and methomyl which is methomyl(s-methyl N-[methylcarbamoyl]oxy) thioacetimidate the graph being compound vs. house fly specks per trap.
Figure 6:
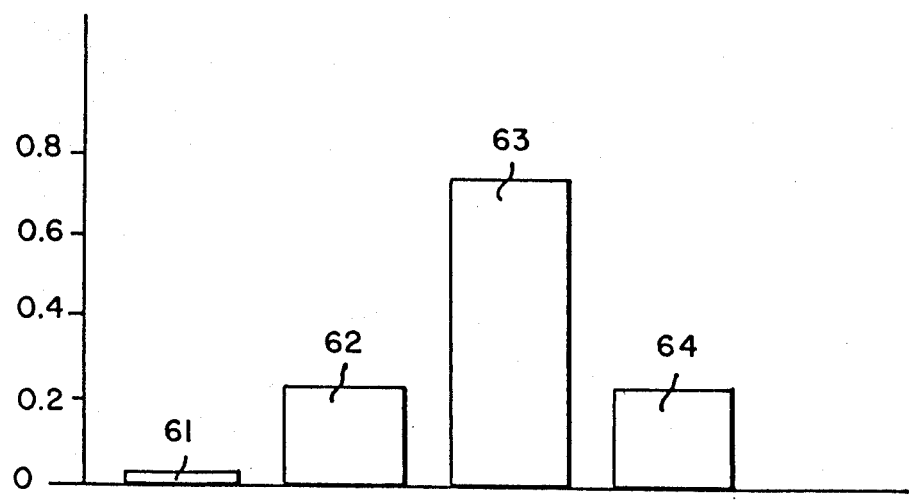
FIG. 6 is a bar graph showing field trial tests of attractants for Stored Products Moths comparing methylisoeugenol, n-Dodecanol and 1-(2-butenoyl)-2,6,6-Trimethyl-1,3-Cyclohexadiene and GOLDEN MALRIN ®, the graph being Stored Products Moths per trap vs. compound.

FIGS. 5 and 6 indicate the results of field trial tests using the apparatus set forth in FIGS. 1, 2, 3 and 4.

Figure 2:
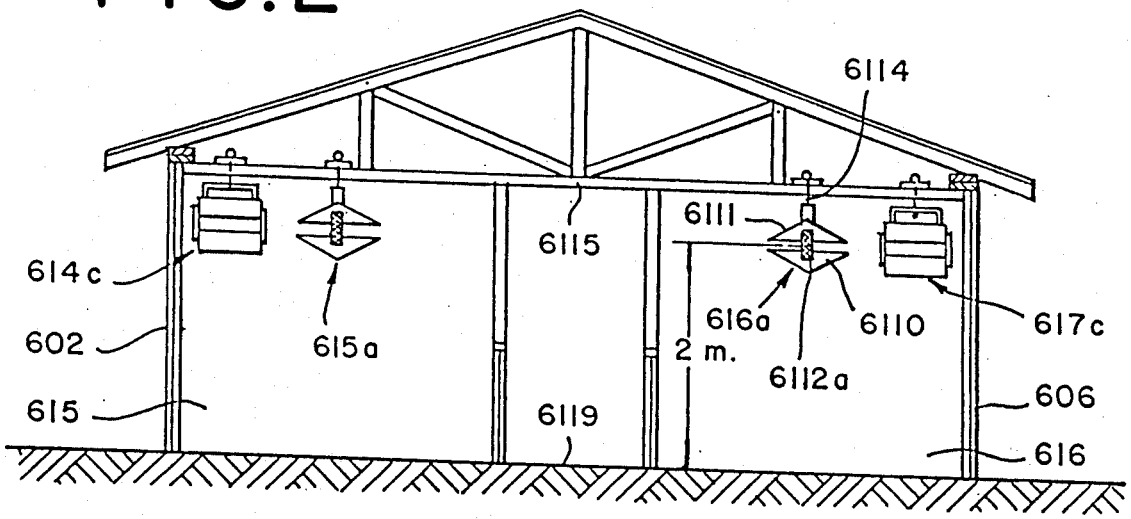
FIG. 2 is a cut-away side elevation view (schematic) indicating the positioning of sticky traps in a test barn taken along lines 2—2 of FIG. 1.
Figure 3:
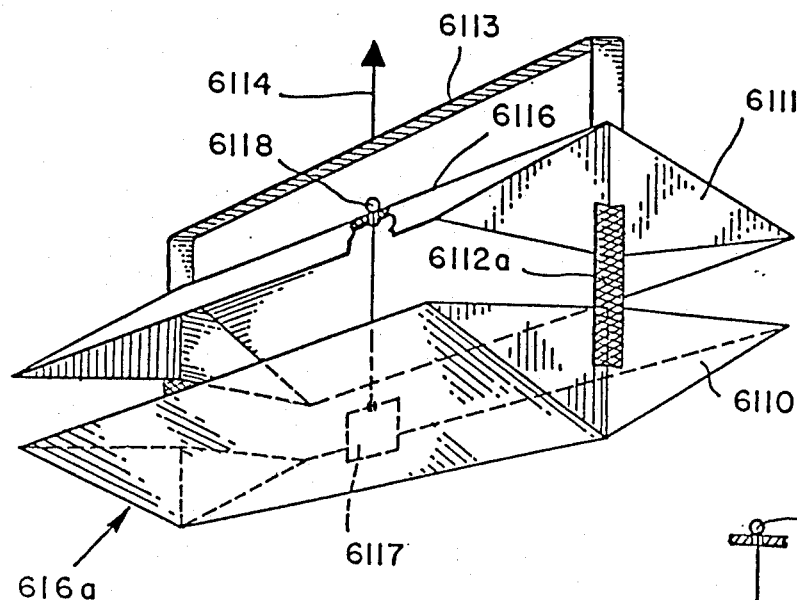
FIG. 3 is a perspective schematic view of a test sticky trap showing the positoning of the slow release material suspended inside of the trap structure.
Figure 4:
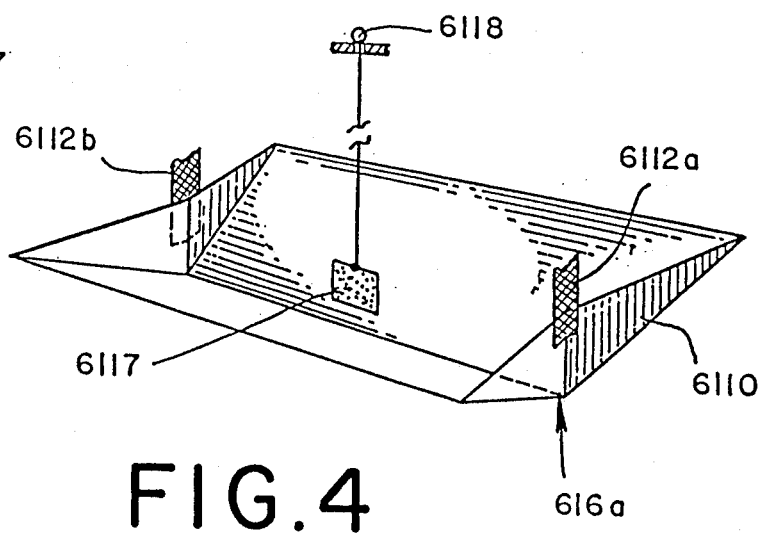
FIG. 4 is a cut-away section in perspective of the sticky trap system of FIG. 3.

FIG. 5 is a series of bar graphs for field trial tests of the attractants methyl-isoeugenol, n-Dodecanol, 1-(2-Butenoyl)-2,6,6-Trimethyl-1,3-Cyclohexadiene and GOLDEN MALRIN ® for house fly speck counts inside of the traps indicated by reference numeral 6117. Thus, the bar graph indicated by reference numeral 52 is the bar graph for methyl-isoeugenol insofar as it attracts *Musca domestica L.* (Diptera:Muscidae) inside of such traps as trap 616a in FIGS. 3 and 4, the house fly specks being located on tray 6110 in FIGS. 3 and 4. Tray 6110 is also shown in FIG. 2. The bar graph indicated by reference numeral 53 in the bar graph for n-Dodecanol insofar as it attracts *Musca domestica L.* (Diptera:Muscidae). The bar graph indiated by reference numeral 51 is the bar graph for GOLDEN MALRIN ® (insofar as it attracts *Musca domestica L. (Diptera:Muscidae). The bar graph indicated by reference numeral 54 is the bar graph for* 1-(2-Butenoyl)-2,6,6-

Trimethyl-1,3-Cyclohexadiene insofar as it attracts *Musca domestica L.* (Diptera:Muscidae). As stated, supra, FIG. 5 is a graph of fly specks/trap vs compound. Thus, the methyl-isoeugenol in FIG. 5 gives rise to an attractancy of *Musca domestica L.* (Diptera:Muscidae) of 12.25 fly specks/trap; the n-Dodecanol gives rise to an attractancy of 17.25 fly specks/trap; and the 1-(2-Butenoyl)-2,6,6-Trimethyl-1,3-Cyclohexadiene gives rise to an attractancy of 29.5 fly specks per trap; and the GOLDEN MALRIN ® gives rise to only 0.75 fly specks per trap.

FIG. 6 is a series of bar graphs of field trial tests of the attractants methyl-isoeugenol, n-Dodecanol, 1-(2-Butenoyl)-2,6,6-Trimethyl-1,3-Cyclohexadiene and GOLDEN MALRIN ® with respect to attractancy for Stored Products Moths. The bar graph indicated by refrence numeral 64 is the bar graph for the attractancy of Stored Products Moths for 1-(2-Butenoyl)-2,6,6-Trimethyl-1,3-Cyclohexadiene. The bar graph indicated by reference numeral 63 in the bar graph for attractany of Stored Products Moths for n-Dodecanol. The bar graph indicated by reference numeral 62 is the bar graph for attractancy of Stored Products Moths using methyl-isoeugenol. The bar graph indicated by reference numeral 61 is the bar graph for attractancy of Stored Products Moths by GOLDEN MALRIN ®.

Figure 7:
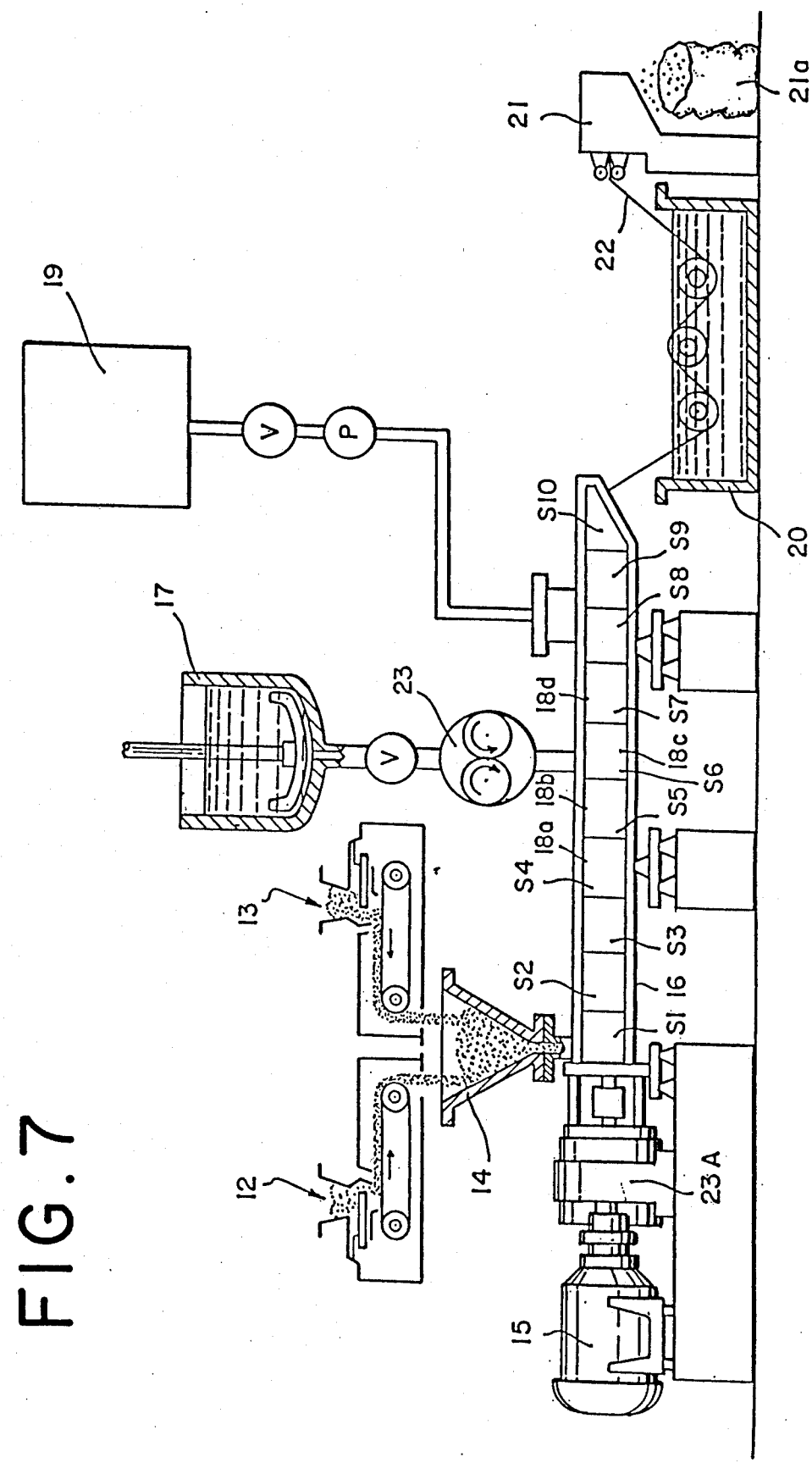
FIG. 7 is a cut-away side elevation schematic diagram of a screw extruder during the compounding of a resin with the insect attractants methyl-isoeugenol, n-Dodecanol or 1-(2-Butenoyl)-2,6,6-Trimethyl-1,3-Cyclohexadiene or combinations thereof while simultaneously adding foaming agent into the hollow portion of the barrel of the extruder and incorporates the pelletizing apparatus used in pelletizing the extruded foamed tow product produced as a result of the extrusion operation.

FIG. 7 is a schematic cut-away elevation diagram of an extrusion and pelletizing apparatus useful in carrying out a process of our invention during the operation of said apparatus whereby the insect attractant is incorporated into a polymer such as a polyethylene. Motor 15 drives the extruder screws located at 23A in barrel 16, the extruder being operated at temperatures in the range of about 150° C. up to about 250° C. At the beginning of the barrel resin at source 12 together with additives, e.g., processing aids and densifiers at location 13 is added via addition funnel 14 into the extruder. Simultaneously (when the operation reaches "steady state"), insect attractant, methyl-isoeugenol, n-Dodecanol, 1-(2-Butenoyl)-2,6,6-Trimethyl-1,3-Cyclohexadiene or mixtures of methyl-iso-eugenol and n-Dodecanol, methyl-isoeugenol and 1-(2-Butenoyl)-2,6,6-Trimethyl-1,3-Cyclohexadiene, n-Dodecanol and 1-(2-Butenoyl)-2,6,6-Trimethyl-1,3-Cyclohexadiene or methyl-isoeugenol, n-Dodecanol and 1-(2-Butenoyl)-2,6,6-Trimethyl-1,3-Cyclohexadiene is added to the extruder at one, two or more barrel segments S-3, S-4, S-5, S-6, S-7 and S-8 of the extruder (which may be a twin screw or single screw extruder) at locations 18a, 18b, 18c and 18d (for example) by means of gear pump 23 from source 17. From source 19 into barrel segments S-5, S-6, S-7, S-8, S-9 and S-10, a gaseous or liquid blowing agent, e.g., nitroen, carbon dioxide and the like as described, supra, are added simultaneously with the addition of the insect attractant, e.g., methyl-isoeugenol, n-Dodecanol, 1-(2-Butenoyl)-2,6,6-Trimethyl-1,3-Cyclohexadiene or combinations of methyl-isoeugenol, n-Dodecanol and/or 1-(2-Butenoyl)-2,6,6-Trimethyl-1,3-Cyclohexadiene. The feed rate range of resin is about 80–300 pounds per hour. The feed rate range of the insect attractant is between 1 and 35% of the feed rate range of the resin. The blowing agnt range is such that the pressure of the gas or the pressure over the liquid being fed into the extruder is between about 50 and 200 psig if, inded, blowing agent is added. If desired, the extruded ribbon or cylinder may be passed through water bath 20 and pelletized 21 into collection apparatus 21a.

Figure 8:
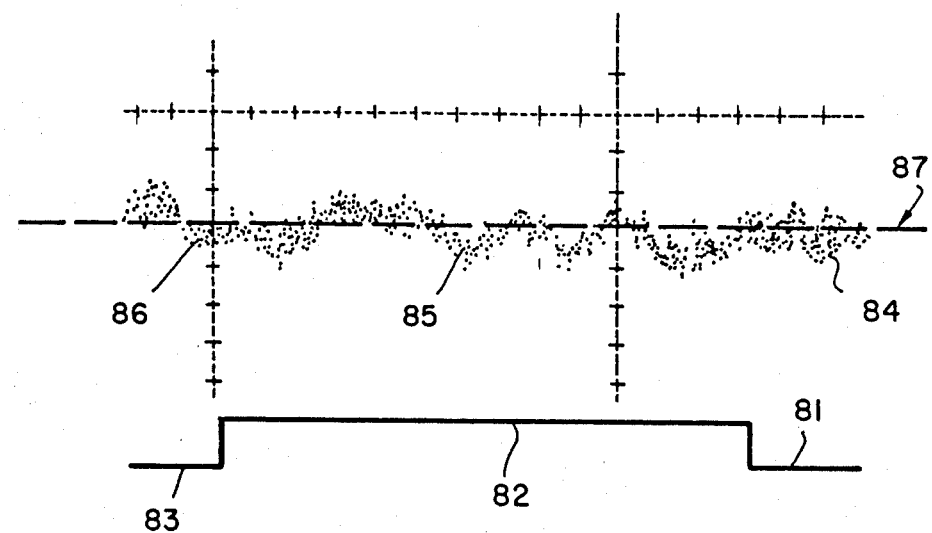
FIG. 8 is a graph of neural signal vs time recorded from the antennal lobe of the *Musca domestica* L. (Diptera:Muscidae) (house fly) using the attractant methyl-isoeugenol as the stimulus.

FIG. 8 sets forth the neural signal recorded from the antennal lobes of the *Musca domestica L.* (Diptera:Muscidae) using methyl-isoeugenol having the structure:

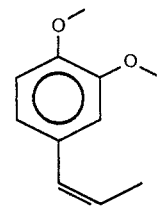

Figure 9:
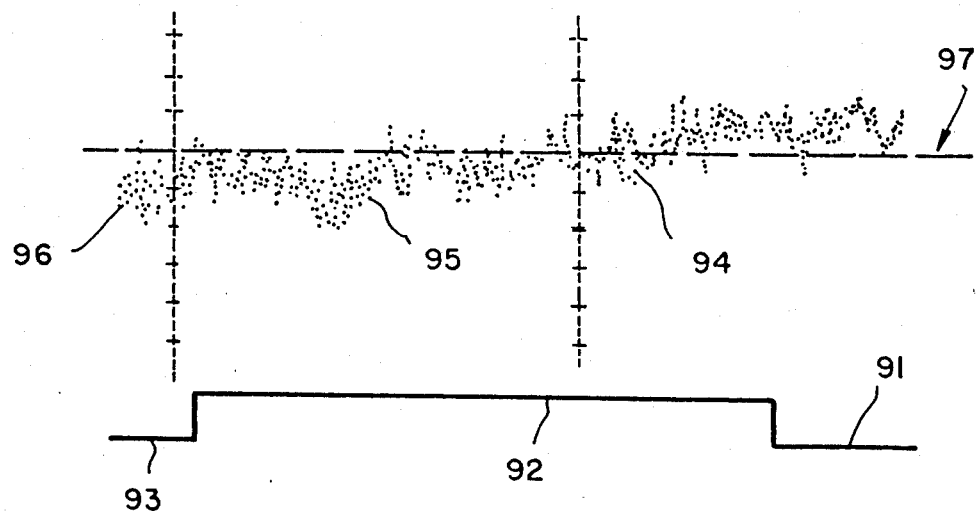
FIG. 9 is a graph of neural signal vs time recorded from the antennal lobe of the house fly (*Musca domestica* L. (Diptera:Muscidae)) using the attractant called "extract of used fly rearing media" (mixture of manures, alfalfa and baking soda) as the stimulus.

FIG. 9 is a graph showing neural signal vs time recorded from the antennal lobe of the *Musca domestica L.* (Diptera:Muscidae) using the attractant called "Extract of used fly rearing media" (mixture of manures, alfalfa and baking soda) as the stimulas. The graphs of FIGS. 8 and 9 are both obtained using apparatus as set forth in FIG. 10.

Figure 10:
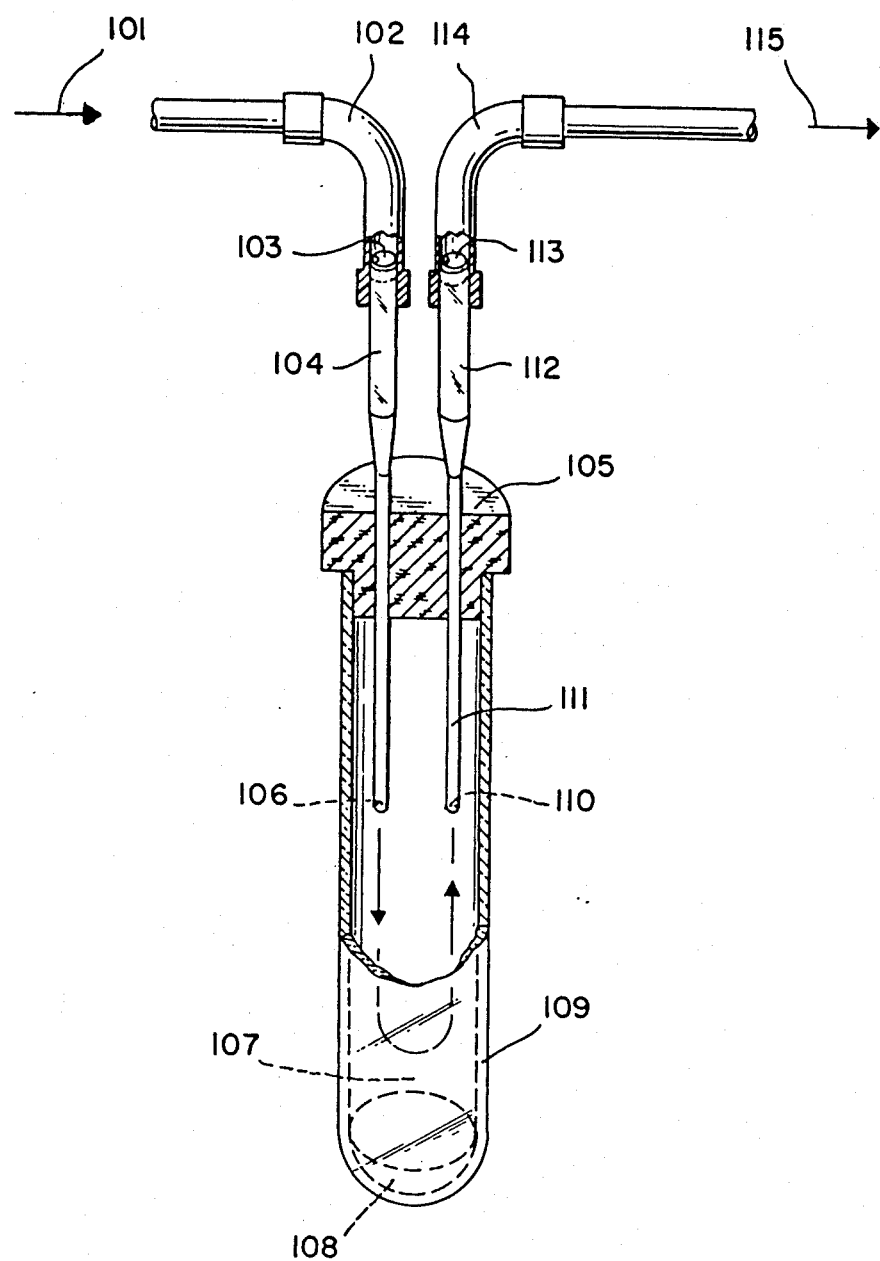
FIG. 10 is a perspective view of the odor delivery system used to supply odor to the house fly (*Musca domestica* L. (Diptera:Muscidae)) when collecting data from the electrophysiological study of the neural correlates of attraction and repulsion in the house fly (*Musca domestica* L. (Diptera:Muscidae)).

FIG. 10 is a diagram in perspective, of a odor delivery system used to supply such materials as methyl-isoeugenol to the fly. When applying the attractant or repellent to be tested to the fly, air from a pressurized air tank is fed through line 101 at location 102 through valve 103 through tube 104 through orifice 106 into the tube 109 containing the media to be tested, e.g., methyl-isoeugenol, indicated by reference numeral 108. The headspace 107 over the media 108 will thus include molecules of air as well as the material to be tested, e.g., methyl-isoeugenol. The resulting mixture of air and attractant or repellent is then passed through orifice 110 through the tube 111-112 past valve 113 through tube 115 (at location 114) to the location where the fly *Musca domestic L.* (Diptera:Muscidae)) reactions are being measured. Tubes 104 and 112 are held in place by holder 105.

Hence, the neural signal in FIG. 8 is set forth and is shown using reference numerals 84, 85 and 86 and the passage or treatment period is shown using reference numerals 81, 82 and 83. Reference numerals 81 and 83 show no passage of test material, e.g., methyl-isoeugenol. The neural signal recorded when no passage of test material takes place is set forth at 84 and 86 (respectively for periods 81 and 83). The neural signal recorded when test material is used to treat the *Musca domestica L.* (Diptera:Muscidae) is set forth at reference numeral 85. The base line for the neural signal recoreded from the antennal lobe using methyl-isoeugenol is indicated by reference numeral 87. The lack of any change from the base line during treatment (82) is indicative of the fact that the methyl-isoeugenol is a strong attractant for *Musca domestica L.* (Diptera:Muscidae).

Referring to FIG. 9, FIG. 9 sets forth the neural signal recorded from the antenal lobe of *Musca domestica L.* (Diptera:Muscidae) using the attractat called "extract of used fly rearing media" as described, supra. Passage of the attractant to the *Musca domestica L.* (Diptera:Muscidae) is indicated at reference numeral 92 whereas referene numerals 91 and 93 indicate no passage of the treating material to be tested. When passage of the test material takes place, the neural signal is indicated at reference numeral 95. When there is no passage of the test material, the neural signal is indicated at reference numeral 96 and at reference numeral 94. Reference numeral 97 is the base line for the neural signal recorded from the antennal lobe using the attractant called "extract of used fly rearing media".

The house flies used for this study were supplied from a laboratory colony at the medical and veterinary entomology laboratory at the University of Florida. A female, 3-7 day old fly was restrained on a standard microscope slide using the following technique. The fly's wings were clipped off near the base in order to facilitate handling. The fly was then glued to the microscope slide, dorsal side down, using Super glue. Ski wax was melted around the head capsule to immobilize the head during electrode penetration. The slide was then placed under a dissecting microscope to enable a more accurate placement of the electrode. Microcapillary electrodes (tip O.D. 1-5 mm) were filled with an ionic fluorescent solution which served the dual purpose of a conducting solution as well as marking the recording site. The ionic solution contained Lucifer yellow CH, a superfluorescent lithium salt of 3,6-disulphonate 4-aminonaphthalimide (Stewart, W. W. 1978 "Functional connections between cells as revealed by dye-coupling with a highly fluorescent naphthalimide tracer" Cell 14:741-759), which is taken up by depolarizing neurons via induced endocytosis (Wilcox and Franceschini, N. 1984 "Illumination induces dye incorporation in photoreceptor cells" Science (Washington, D.C.) 225:851-854.).

The active electrode was positioned in the selected spot using Nashike micromanipulators with remote hydraulic drive. Areas for electrophysiological study were located using (Strausfeld, N.J. 1978 "Atlas of an insect brain", Springer-Verlag:Berlin) (1976) detailed anatomical study of the house fly brain, which includes a three-dimensional coordinate system. Subsequent gross dissections showed that with much practice, individual lobes on the brain could be penetrated with repeatable accuracy.

The indifferent electrode was placed either in the head capsule or thorax. The preferred position was the thorax as this places the electrode out of the way. However, care must be taken not to place the indifferent electrode in the ventral nerve cord as this results in extraneous nerve signals.

In placing the active elecrode, it was necessary to prick the cuticle with a minuten pin in order to prevent deformation of the head capsule as the electrode penetrated. This method minimized damage to the underlying neural tissue.

Nerve signals were preamplified with custom neutral amplifirs at 100X and then displayed on a Nicolet 3091 oscilloscope. The same signal was simultaneously sent to a Dianachart smart recorder/data logger to obtain a hard copy of the neural signal.

The olfactory stimulus was initially supplied using the technique developed by (Kauer, J. S.; Shepherd, G. M. 1975 "Olfactory stimulation and monitored sftep pulses of odor", Brain Res. 85:108-113) and (Getchel, T. V.; Shepherd, G. M. 1978 "Responses of olfactory receptor cells to step pulses of odor at different concentrations in the salamander", J. Physiol. 282:521-540) which uses three concentric pipettes, one to apply the odor and the other two to exhaust the odor. However, this system proved to be too bulky for house flies due to their small size, as it was not possible to form three concentric pipettes which were small enough not to be bulky, but not so small as t restrict air flow.

Consequently, a system was developed which used pressurized air to deliver the odor and an exhaust system was built around the entire set up. The delivery system was a test tube containing 2 ml of odor extract, stoppered, and with two disposable pipettes through the rubber stopper through the rubber stopper (as is shown in FIG. 10). One pipette 104 was attached to a pressurized air tank and the other pipette 112 was attached to a tygon tube terminating in a capillary tube which could be positioned directly in front of the fly's antennae.

Odor delivery (e.g., methyl-isoeugenol) was controlled with a valve 113 so that abrupt onset of the stimulus was possible. Each stimulus was approximately 4-5 seconds in duration. A minimum of 15 minutes was used between odor stimulus to allow the previous odor to be completely exhausted from the area.

What is claimed is:

1. A method of attracting *Musca domestica* L. (Diptera Muscidae) to an insect trap comprising the step of exposing the environment surrounding said trap to an insect attractant containing polymer which consists of a mixture of a polymer which is compatible with said attractant and from about 1% up to about 45% by weight of said polymer of an attractant selected from the group consisting of:
   (i) methyl isoeugenol;
   (ii) n-Dodecanol; and
   (iii) a mixture of methylisoeugenol and n-Dodecanol.

2. The method of claim 1 wherein the composition of matter is methyl-isoeugenol.

3. The method of claim 1 wherein the composition of matter is n-Dodecanol.

4. The method of claim 1 wherein the composition of matter is a mixture of methyl-isoeugenol and n-Dodecanol.

5. A method of attracting stored product moths to an insect trap comprising the step of exposing the environment surrounding said trap to an insect attractant containing polymer which consists of a mixture of a polymer which is compatible with said attractant and from about 1% up to about 45% by weight of said polymer of an attractant selected from the group consisting of:
   (i) methyl isoeugenol;
   (ii) n-Dodecanol; and
   (iii) a mixture of methylisoeugenol and n-Dodecanol.

6. The method of claim 5 wherein the composition of matter is methylisoeugenol.

7. The method of claim 5 wherein the composition of matter is m-Dodecanol.

8. The method of claim 5 wherein the composition of matter is a mixture of methylisoeugenol and n-Dodecanol.

* * * * *